United States Patent [19]

Kurze et al.

[11] Patent Number: 4,801,300
[45] Date of Patent: Jan. 31, 1989

[54] SINGLE PART BIOCOMPATIBLE HIP-JOINT SOCKET MOORABLE WITHOUT CEMENT

[75] Inventors: Peter Kurze, Oberlichtenau; Klaus Rabending, Taura; Waldemar Krysmann, Karl Marx Stadt; Peter Daniel, Karl Marx Stadt; Rainer Morgenstern, Karl Marx Stadt; Wilfried Wehner, Karl Marx Stadt; Manfred Polster, Karl Marx Stadt, all of German Democratic Rep.

[73] Assignee: Technische Universitaet Karl-Marx-Stadt, Karl Marx Stadt, German Democratic Rep.

[21] Appl. No.: 137,392

[22] Filed: Dec. 23, 1987

Related U.S. Application Data

[63] Continuation-in-part of Ser. No. 19,408, Feb. 26, 1987, abandoned.

[30] Foreign Application Priority Data

Mar. 12, 1986 [DD] German Democratic Rep. .................................. 2878010

[51] Int. Cl.[4] .............................................. A61F 2/34
[52] U.S. Cl. ........................................ 623/22; 623/16; 128/92 YQ; 128/92 YG; 427/2; 204/38.6
[58] Field of Search ............................ 623/22, 16–21, 623/23; 128/92 YQ, 92 YG, 92 YR, 92 W; 433/173–176, 201.1, 202.1, 206, 207; 204/38.6, 42; 427/2

[56] References Cited

U.S. PATENT DOCUMENTS

| | | | |
|---|---|---|---|
| 4,146,936 | 4/1979 | Aoyagi et al. | 433/176 X |
| 4,262,369 | 4/1981 | Roux | 623/22 X |
| 4,365,358 | 12/1982 | Judet, deceased et al. | 623/22 |
| 4,483,678 | 11/1984 | Nishio et al. | 433/201.1 |
| 4,599,085 | 7/1986 | Riess et al. | 623/16 |
| 4,676,799 | 6/1987 | Legrand | 623/22 |

FOREIGN PATENT DOCUMENTS

| | | | |
|---|---|---|---|
| 2314708 | 10/1974 | Fed. Rep. of Germany | 623/22 |
| 2318396 | 10/1974 | Fed. Rep. of Germany | 623/22 |
| 2751537 | 5/1979 | Fed. Rep. of Germany | 623/22 |
| 3130732 | 5/1983 | Fed. Rep. of Germany | 623/22 |

Primary Examiner—Richard J. Apley
Assistant Examiner—Alan W. Cannon
Attorney, Agent, or Firm—Jordan and Hamburg

[57] ABSTRACT

The invention relates to a single-part, biocompatible hip-joint socket moorable without cement, which hip-joint socket can be used universally in combination with hip-joint endoprostheses and is especially suitable for the treatment of dysphasia hips. The joint socket is made of Ti or Ta metals forming a barrier layer or of alloys thereof and is provided with a perforated flange ring for screwing to the pelvic bone, as well as being provided over its entire surface with specific function characteristic oxide layers containing bioactivators. For the implantation of the hip-joint socket, there are not required any special operating instructions, and additional operations, such as pelvic osteotomies, plasties of the roof of the acetabulum and repeated operations are prevented or minimized.

11 Claims, 3 Drawing Sheets

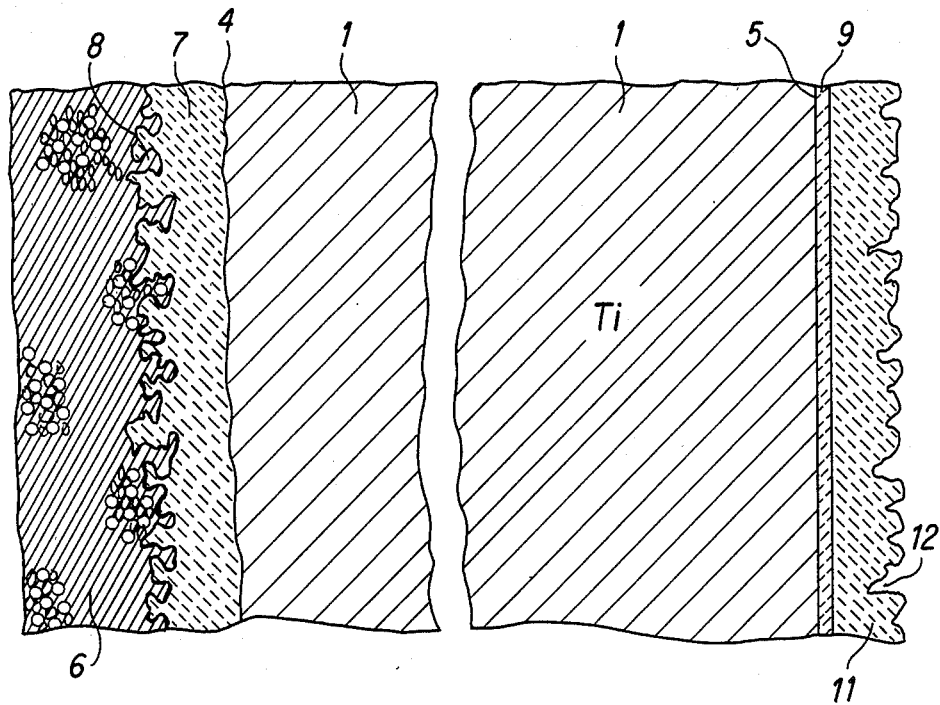

SINGLE PART BIOCOMPATIBLE HIP-JOINT SOCKET MOORABLE WITHOUT CEMENT

REFERENCE TO RELATED APPLICATION

This is a continuation-in-part of application Ser. No. 019,408, filed Feb. 26, 1987 now abandoned.

This invention relates to a single-part biocompatible hip-joint socket moorable without cement for use as an endoprosthesis.

Hip-joint sockets for surgical use are made of plastics, preferably polyethylene or metal combined with polyethylene or solid ceramics.

Polyethylene used for hip-joint sockets (DE-OS No. 3200340, CH-P648747) in its compactness has a relatively good biocompatibility. It is known, however, that abrasions which are caused by the action of the joint head can be resorbed only with difficulty or not at all by the human body. Thus, there can occur inflammations which can require further operations. In spite of the moorage profiles mounted on the joint socket consisting of polyethylene (CH-P No. 648747) there is attained only an insufficient long-term stabilization.

More favorable is the positive moorage to the bone attained by two-component hip-joint sockets made of metal combined with polyethylene (DE-OS No. 231473). But the above-mentioned disadvantage of the utilization of polyethylene still remains.

In AT-P No. 337885 is proposed an implantable artificial joint substitute made of ceramic, whereby the head and the socket are made of ceramic. In spite of the good biocompatibility of the ceramic, the resorbability of the abrasion and the favorable sliding matches, geometrically dependent disadvantages remain as in all of the above-mentioned systems. These are, in particular, the large dimensions of the joint sockets in relation to the anatomy of the pelvis.

Very often additional operations, such as pelvic osteotomies according to Chiari or plasties of the roof of the acetabulum according to Harris, are necessary in order to attain a safe moorage. Dysplasia hips cannot be treated with the solutions offered up to now.

SUMMARY OF THE INVENTION

The object of the invention is to develop a universally utilizable hip-joint socket having a high biocompatibility, as well as safe moorage and, thus, a long residence time, and which can be implanted with known surgical techniques, in order to be able to reduce repeated operations due to loosening and inflammations of joint sockets.

Another object of this invention is to develop a single-part, biocompatible hip-joint socket moorable without cement, i.e., a mechanically stable hip-joint socket which is as small as possible, adjusted to the anatomy of the human pelvis, safely moorable and provided with good sliding properties.

According to the invention, prior art problems are solved in that a single-part joint-socket is shaped from a metal such as titanium or tantalum which forms a barrier layer, or of medically acceptable and known alloys thereof such as $TiAl_6V_4$. The joint socket is provided at least over $\frac{2}{3}$ of the circumference with a perforated flange ring for the mooring by implant screws. The surface situated facing the pelvic bone consists of a characteristic oxide layer with bottle-shaped pores. This layer has $TiO_x$ or $Ta_2O_5$ as a main component and a calcium phosphate content of more than 40%. The surface of the socket situated on the side of the joint bears a two-layer composite whose layer over the metal is a mechanically compacted, finest-pored characteristic oxide layer having $TiO_x$ or $Ta_2O_5$ as a main component and whose layer thereupon is a fine-pored, abrasion-resistant characteristic oxidic sliding layer having $TiO_x$ or $Ta_2O_5$ as a main component and 10–30% calcium phosphate and containing cylinder-shaped or funnel-shaped pores.

The advantages of the solution according to the invention are that there is a minimization of the dimensions of the joint socket while safeguarding a high mechanical stability. In this way, a reliable moorage in the dysplastic hip-joint region is also attained. The implantation does not require any additional implantation instrumentarium, and requires neither bone cement nor any additional operations such as pelvic osteotomies or plasties of the roof of the acetabulum. The special layer construction guarantees a high biocompatibility. The layer situated facing the pelvic bone has a bone-growth-promoting effect and such a geometrical structure that the growing tissue moors in the bottle-shaped pores like press-buttons.

The two layer composite of the socket's surface situated on the side of the joint, on the one hand, minimizes the diffusion of metal ions and abrasion and, on the other hand, creates favorable conditions for the storage and transport of synovial fluid. Moreover, there are present lubricating surface films consisting of phosphates or oxides of which it has been proven that their abrasions are resorbed by the organism without any problems. The solution according to the invention enables a long-term residence time in the human body and prevents repeated operations dependent on the implant. In this way it is possible to provide younger patients with a hip-joint endoprosthesis.

BRIEF DESCRIPTION OF THE DRAWINGS

The invention will be better understood by reference to the accompanying drawings, in which:

FIG. 3 is a magnified sectional schematic view illustrating the external surface of the hip joint socket of FIG. 1 anchored with the bone tissue of the pelvis;

FIG. 4 is a magnified sectional schematic view illustrating the internal surface of the hip joint socket of FIG. 1.

DETAILED DESCRIPTION OF THE PREFERRED EMBODIMENTS

The invention will be explained hereinafter in greater detail by an exemplified embodiment, illustrated in FIGS. 1 to 6.

Figure 1:
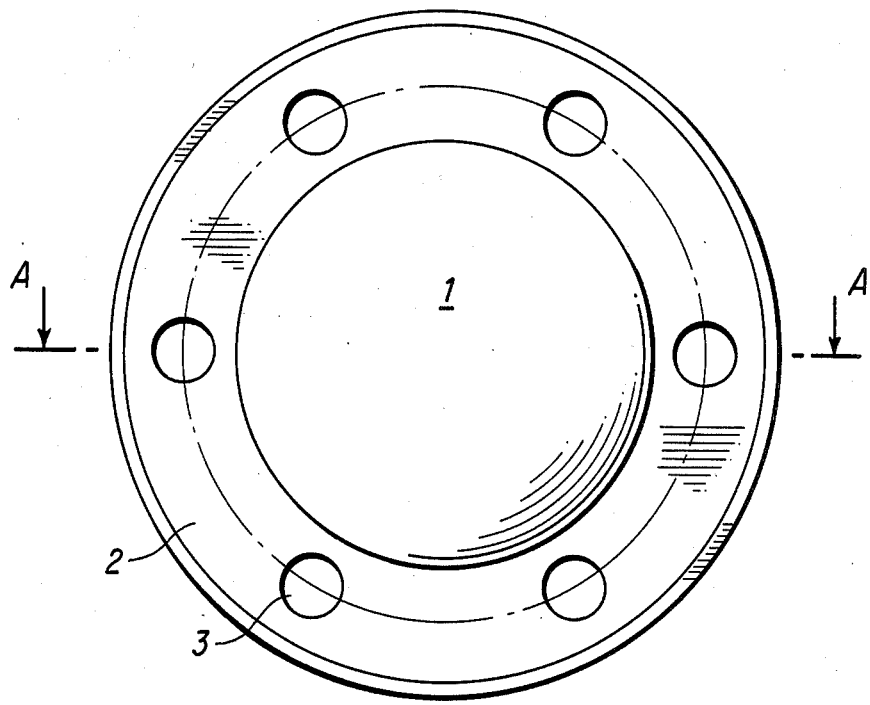
FIG. 1 is a top plan view of one embodiment of the hip joint socket of the present invention.
Figure 2:
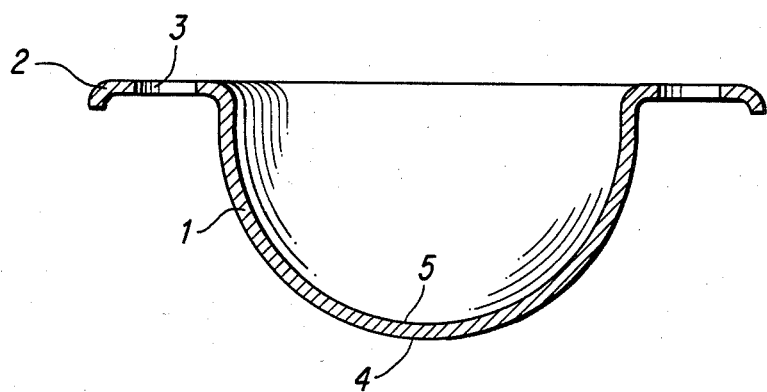
FIG. 2 is a sectional view taken along the line A—A of FIG. 1.

As shown in FIGS. 1 and 2, a spherical hip-joint socket 1 made of purest titanium sheet having an inside radius of 16 mm and a total wall thickness of 1.08 mm is provided with a flange ring 2 or 8 mm width which envelops at least $\frac{2}{3}$ of the circumference. This flange ring has at least four uniformly distributed boreholes 3 of 4.5 mm.

As shown in FIG. 3, surface 4 situated facing pelvic bone tissue 6 bears an ANOF oxide layer 7 which is 20 μm thick and contains pores 8. Layer 7 has a calcium phosphate content of 45% at the peripheral zone and a relative surface of 140%. "Relative surface" means the relationship or ratio of the surface of layer 7 which is effective in the micro range and which is greatly magnified by the pores 8, in relation to the macroscopic measurable metal surface 4 before coating. 25% of the pores 8 are bottle-shaped. ANOF oxide layer 7 is obtained by the method of anodic oxidation using spark discharge.

"Bottle-shaped pores" refers to pores which, in comparison to a relatively wide body part, have a narrow neck part and therefore also a narrow pore entrance. The inside diameter of the "container" part can amount to a multiple of the inside diameter of the pore entrances.

As shown in FIG. 4, surface 5 of the socket situated facing the hip joint bears a 2 μm thick mechanically compacted finest-pored $TiO_x$ oxide layer 9 over the metal. Upon this oxide layer 9 is an ANOF oxide gliding layer 11 of 8 μm thickness having pores 12 and a calcium phosphate content of 15% at the peripheral zone. The relative surface is greater than 150%. The pores 12 are predominantly funnel-shaped and also cylinder-shaped.

"Cylinder-shaped pores" refers to pores whose inside diameter is approximately equal from the pore entrance to the pore bottom. "Funnel-shaped pores" refers to pores which have at the pore bottom a smaller inside diameter than at the pore entrance.

Figure 6:
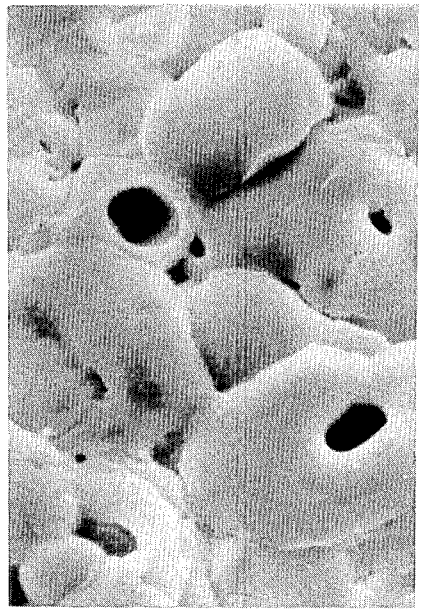
FIGS. 5, 6 and 7 are REM microphotographs of the surface morphology of the hip joint socket of the present invention.
Figure 7:
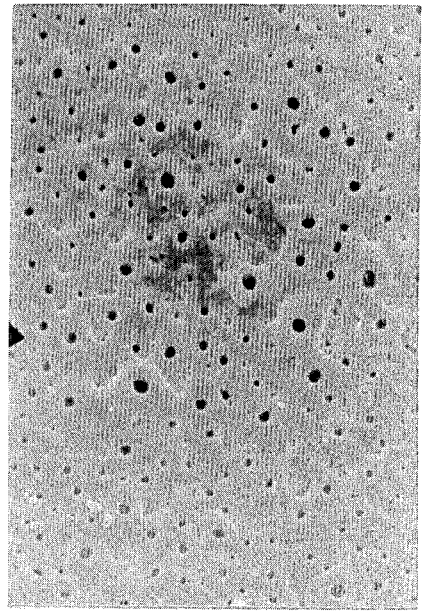

The REM photographs show on a scale of 1000:1 and 3000:1 the bottle-shaped pore layer (FIGS. 5 and 6, respectively) and on a scale of 1000:1 the cylinder-shaped and funnel-shaped pore layer (FIG. 7).

Figure 5:
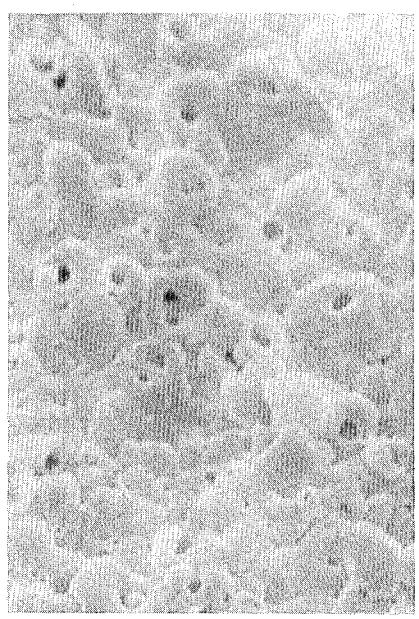

In FIG. 5, the surface of the bottle-shaped pore layer can be seen, which is more heavily textured than the surface in FIG. 6. The pore entrances have an inside diameter of 3 microns; however, depending on the coating conditions and layer thickness, they can be as much as about 10 microns. It can furthermore be seen that a snap-fastener-like anchoring to the contiguous bone tissue is achieved by the fact that the bone tissue grows fully around the socket-like particles and partially into the pores, respectively.

The cylinder-shaped and funnel-shaped pore layer, however, is less textured at the surface as can be seen from FIG. 7. The pore entrances have an inside diameter of about 1 micron to 3 microns, and are situated mostly in the center of relatively planar slip surfaces. The socket-like surface structure, such as that which the bottle-shaped pore layer has, is here lacking. Funnel-shaped pores and cylinder-shaped pores always occur together. They do not differ in their function of storing the joint fluid.

Layer thickness, porosity, pore shape and pore size are determined by the process parameters in the coating. The bottle-shaped pore layer (FIGS. 5 and 6) is formed by the ANOF process in an electrolyte containing fluoride, phosphate and borate under direct-current conditions. The cylinder-shaped and funnel-shaped pore layers are obtained also by the ANOF process in an electrolyte containing only calcium and phosphate under pulsed-current conditions.

The raw hip-joint socket can be produced by deep drawing of the sheet metal and subsequent machine microfinishing of the internal surface 3 of the joint socket. The external surface 4 of the spherical segment 1 is roughened in a mechanical way. The holes 3 are punched. The layer construction is obtained as described using the ANOF (anodic oxidation under spark-discharge) method, i.e., separately externally and internally individually in a one-step process according to DD-WP 156003 or DD-WP 160749.

Eight weeks after the implantation of the joint socket together with an endoprosthesis bearing a ceramics ball head, the healing-in process of the implant was completed and the implant was released for loads without supporting stocks.

What we claim is:

1. A single-piece biocompatible hip-joint socket moorable without cement for engaging a hip joint and a pelvic bone comprising a spherical joint socket having a circumference, a convex surface for facing the pelvic bone and a concave surface for facing the hip joint, said joint socket being made of a metal forming a barrier layer, and a perforated flange ring enveloping at least ⅔ of the circumference of said joint socket for the moorage, wherein said convex surface consists of an exposed surface of a porous oxide layer comprising $TiO_x$ or $Ta_2O_5$ and having a calcium phosphate content at and adjacent the exposed surface thereof of at least 40%, and said concave surface consists of an exposed surface of the second layer of a two-layer composite comprising a first layer adjacent said concave surface of a mechanically compacted, finest-pored oxide layer comprising $TiO_x$ or $Ta_2O_5$ and a second layer overlying said first layer of a fine-pored, abrasion-resistant, oxide sliding layer comprising $TiO_x$ or $Ta_2O_5$ and having a calcium phosphate content at and adjacent the exposed surface thereof of 10–30%.

2. A single-piece, biocompatible hip-joint socket moorable without cement according to claim 1, wherein said joint socket consists of a sheet of metal forming the barrier layer.

3. A single-piece, biocompatible hip-joint socket moorable without cement according to claim 1, wherein said joint socket consists of a sintered metal body forming the barrier layer.

4. A single-piece, biocompatible hip-joint socket moorable without cement according to claim 1, wherein the metal forming the barrier layer is titanium.

5. A single-piece, biocompatible hip-joint socket moorable without cement according to claim 1, wherein the metal forming the barrier layer is tantalum.

6. A single-piece, biocompatible hip-joint socket moorable without cement according to claim 1, wherein the metal forming the barrier layer is a titanium alloy.

7. A single-piece, biocompatible hip-joint socket moorable without cement according to claim 1, wherein the metal forming the barrier layer is a tantalum alloy.

8. A single-piece, biocompatible hip-joint socket moorable without cement according to claim 1, wherein the pores of the convex surface oxide layer are bottle-shaped.

9. A single-piece, biocompatible hip-joint socket moorable without cement according to claim 1, wherein the fine pores of the concave surface second oxide layer are funnel-shaped.

10. A single-piece, biocompatible hip-joint socket moorable without cement according to claim 1, wherein the fine pores of the concave surface second oxide layer are cylinder-shaped.

11. A single-piece, biocompatible hip-joint socket moorable without cement according to claim 1, wherein the fine pores of the concave surface second oxide layer are funnel-shaped and cylinder-shaped.

* * * * *